United States Patent
Makhynya et al.

(10) Patent No.: US 12,172,144 B2
(45) Date of Patent: Dec. 24, 2024

(54) USE OF SUPERCRITICAL $CO_2$ AS SOLVENT FOR ORGANIC POLYMERS IN A METHOD FOR COATING UREA-CONTAINING GRANULES

(71) Applicants: thyssenkrupp Industrial Solutions AG, Essen (DE); thyssenkrupp AG, Essen (DE)

(72) Inventors: Yevgeny Makhynya, Mülheim (DE); Tarek El Hawary, Holzwickede (DE)

(73) Assignees: thyssenkrupp Uhde GmbH, Dortmund (DE); thyssenkrupp AG, Essen (DE)

( * ) Notice: Subject to any disclaimer, the term of this patent is extended or adjusted under 35 U.S.C. 154(b) by 927 days.

(21) Appl. No.: 17/254,117

(22) PCT Filed: Jun. 14, 2019

(86) PCT No.: PCT/EP2019/065758
§ 371 (c)(1),
(2) Date: Dec. 18, 2020

(87) PCT Pub. No.: WO2019/243204
PCT Pub. Date: Dec. 26, 2019

(65) Prior Publication Data
US 2021/0268460 A1 Sep. 2, 2021

(30) Foreign Application Priority Data
Jun. 20, 2018 (DE) .................... 10 2018 210 030.6

(51) Int. Cl.
*B01J 2/00* (2006.01)
*B05D 1/02* (2006.01)
(Continued)

(52) U.S. Cl.
CPC .............. *B01J 2/006* (2013.01); *B05D 1/025* (2013.01); *C07C 273/10* (2013.01);
(Continued)

(58) Field of Classification Search
CPC ..... Y02P 20/129; Y02P 20/54; G03G 15/234; F25J 1/0027; F25J 2210/80;
(Continued)

(56) References Cited

U.S. PATENT DOCUMENTS

| 4,019,890 A | 4/1977 | Fujita |
| 5,171,613 A | 12/1992 | Bok et al. |

(Continued)

FOREIGN PATENT DOCUMENTS

| DE | 102005028016 A | 12/2006 |
| EP | 0706821 A | 4/1996 |

(Continued)

OTHER PUBLICATIONS

English Translation of International Search Report issued in PCT/EP2019/065758, dated Oct. 15, 2019.
(Continued)

*Primary Examiner* — Shuangyi Abu Ali
(74) *Attorney, Agent, or Firm* — thyssenkrupp North America, LLC

(57) ABSTRACT

A process may be utilized to coat urea-containing granules with organic polymers. The process may involve compressing gaseous carbon dioxide and condensing the carbon dioxide to obtain liquid carbon dioxide, increasing the pressure and/or the temperature above the critical point of carbon dioxide and obtaining supercritical carbon dioxide, dissolving an organic polymer in the supercritical carbon dioxide to obtain a polymer-containing solution, and mixing the polymer-containing solution with urea-containing granules and lowering the temperature and/or the pressure below the critical point of carbon dioxide and obtaining coated urea-containing granules and gaseous carbon dioxide. In some cases the organic polymer may include biodegradable
(Continued)

polymers, and the polymer-containing solution may contain between 20 to 70% by weight biodegradable polymers.

13 Claims, 2 Drawing Sheets

(51) Int. Cl.
    *C07C 273/10* (2006.01)
    *F25J 1/00* (2006.01)
(52) U.S. Cl.
    CPC .......... *F25J 1/0027* (2013.01); *F25J 2210/80* (2013.01); *F25J 2220/80* (2013.01)
(58) Field of Classification Search
    CPC ...... F25J 2220/80; C07C 273/10; C05G 5/37; C05C 9/005; B05D 1/025; B01J 2/006
    See application file for complete search history.

(56) References Cited

U.S. PATENT DOCUMENTS

| | | | |
|---|---|---|---|
| 5,653,781 A | 8/1997 | Kayaert et al. | |
| 5,766,637 A | 6/1998 | Shine | |
| 2005/0112205 A1* | 5/2005 | Moolman | A61K 47/58 424/487 |
| 2006/0210640 A1* | 9/2006 | Kerkhof | A61K 9/1623 424/489 |
| 2008/0156035 A1* | 7/2008 | Aspelund | F25J 1/004 62/902 |
| 2008/0248954 A1 | 10/2008 | Sanders | |
| 2011/0094277 A1* | 4/2011 | Kilambi | C07C 273/04 977/773 |
| 2016/0144292 A1* | 5/2016 | Crandall | B01D 11/0207 422/255 |
| 2019/0322539 A1 | 10/2019 | Johanning | |

FOREIGN PATENT DOCUMENTS

| | | | |
|---|---|---|---|
| JP | H04-260460 A | | 9/1992 |
| JP | H07-133179 A | | 5/1995 |
| JP | 2000-511110 A | | 8/2000 |
| JP | 2002145691 A | * | 5/2002 |
| JP | 2003-192482 A | | 7/2003 |
| RU | 2104258 C1 | | 2/1998 |
| WO | 9815348 A | | 4/1998 |
| WO | 03082003 A | | 10/2003 |
| WO | 2019063681 A | | 4/2019 |

OTHER PUBLICATIONS

Holleman, Wiberg, Lehrbuch der Anorganischen Chemie [Textbook of Inorganic Chemistry], 102th edition, 2007, p. 894 (ISBN 978-3-11-017770-1).
VDI Wärmeatlas, ISBN 978-3-642-19980-6).
DIN EN ISO 14855-1:2013-04.
ASTM D 5338.
Castia Bastioli, Handbook of Biodegradable Polymers, Rapra Technology Limited, 2005, ISBN: 1-85957-389-4, chapter 5, pp. 145-181.
ISO 14852.
ISO 14851.
ISO 14855 Amendment 1.
EN 13432.
DIN V54900.
ASTM D6002-96.
ASTM D6400-99.
Ullmann's Encyclopedia of Industrial Chemistry, Introduction, 2010, DOI.
Meesen, J., Urea, Ullmann's Encyclopedia of Industrial Chemistry vol. 37, (2012), pp. 658-695.
ASTM D6400-99, Standard Specification for Compostable Plastics, (May 1999).
ASTM D6002-96, Standard Guide for Assessing the Compostability of Environmentally Degradable Plastics, (2002).
DIN V54900-2, Prüfung der Kompostierbarkeit von Kunststoffen, (1998). [translation unavailable].
DIN EN 13432 Berichtigung 2, Verpackung—Anforderungen an die Verwertung von Verpackungen durch Kompostierung und biologischen Abbau, (2007). [translation unavailable].
DIN EN 13432, Packaging—Requirements for packaging recoverable through composting and biodegradation—Test scheme and evaluation criteria for the final acceptance of packaging, (2000). [translation unavailable].
ISO 14851, Determination of the ultimate aerobic biodegradability of plastic materials in an aqueous medium—Method by measuring the oxygen demand in a closed respirometer, (1999).
ISO 14851:1999, Determination of the ultimate aerobic biodegradability of plastic materials in an aqueous medium—Method by measuring the oxygen demand in a closed respirometer, (2005).
ISO 14855:1999(E), Determination of the ultimate aerobic biodegradability and disintegration of plastic materials under controlled composting conditions—Method by analysis of evolved carbon dioxide, (1999).
ISO 14855:1999, Determination of the ultimate aerobic biodegradability and disintegration of plastic materials under controlled composting conditions—Method by analysis of evolved carbon dioxide Amendment 1: Use of activated vermiculite instead of mature compost, (2004 Amendment 1).
ISO 14852:1999(E), Determination of the ultimate aerobic biodegradability of plastic materials in an aqueous medium—Method by analysis of evolved carbon dioxide, (1999).
International Standard ISO 14852:1999, Technical Corrigendum 1, Determination of the ultimate aerobic biodegradability of plastic materials in an aqueous medium—Method by analysis of evolved carbon dioxide, (2005).
Bruno De Wilde, Chapter 5: International and National Norms on Biodegradability and Certification Procedures, pp. 145-181, (2005).
ASTM D5338-15, Standard Test Method for Determining Aerobic Biodegradation of Plastic Materials Under Controlled Composting Conditions, Incorporating Termophilic Temperatures, (2015).
DIN EN ISO 14855-1, Bestimmung der vollständigen aeroben Bioabbaubarkeit von Kunststoff-Materialien unter den Bedingungen kontrollierter Kompostierung—Verfahren mittels Analyse des freigesetzten Kohlenstoffdioxides—Teil 1: Allgemeines Verfahren, (2013). [translation unavailable].

* cited by examiner

USE OF SUPERCRITICAL CO$_2$ AS SOLVENT FOR ORGANIC POLYMERS IN A METHOD FOR COATING UREA-CONTAINING GRANULES

CROSS REFERENCE TO RELATED APPLICATIONS

This application is a U.S. National Stage Entry of International Patent Application Serial Number PCT/EP2019/065758, filed Jun. 14, 2019, which claims priority to German Patent Application No. DE 10 2018 210 030.6, filed Jun. 20, 2018, the entire contents of both of which are incorporated herein by reference.

FIELD

The present disclosure generally relates to processes for coating urea-containing particles with biodegradable polymers and to plant complexes for coating urea-containing particles with biodegradable polymers.

BACKGROUND

In view of the global population growth, the development of flexible and efficient fertilizers is of great and growing importance. Not only the fertilizer itself, i.e. the chemical composition, but also the processing in transportable containers and the application on the field play a role. The granulation to form uniform particles of the same size and condition is certainly of the greatest importance. Important parameters here are low dust formation, strength, low tendency to aggregate, homogeneous size, shelf life and durability. An established granulation technique is, for example, fluidized bed granulation, which has improved particle properties compared to, for example, the prilling and pelleting techniques.

Urea-containing fertilizers account for a very large proportion of global fertilizer production. These water-soluble fertilizers are transformed in the soil into ammonium salts or nitrates and are an important basic fertilizer. These urea-containing fertilizers can be combined with other elements, such as potassium, manganese, phosphates, sulfur, sulfur compounds, selenium, calcium, inter alia.

In addition to good availability of the fertilizer in the soil, good determinability and reproducibility of the nutrient release to the plant is also of great importance. This can lead to an excess of the fertilizer, especially at the beginning of fertilization and in the event of incorrect dosing. This excess can damage the plants and even cause them to die. These losses of fertilizer are also responsible for the problems with soil and groundwater. Coated fertilizer granules are known to solve this problem. As a rule, a core made of fertilizer-containing granules is provided with one or more casings. Depending on the application profile, a very fast dissolution, for example through a water-soluble polymer, such as starch or polyethylene oxide, may take place. If a slower dissolution and release of the fertilizer is desirable, casings made of organic polymers, in particular biodegradable polymer casings, are suitable. The polymer layer behaves like a membrane and makes it possible for water/water vapor to penetrate into the particle. The fertilizers dissolved in the water then leave the remaining "polymer shell" through diffusion and osmosis, and thus make possible a targeted release of the fertilizer to the soil and the plant. The biodegradability of a polymer-containing coating in the soil (for example within a period of approx. 1-2 years) can be determined using DIN EN ISO 14855-1:2013-04 or ASTM D 5338, for example. Depending on the area of application, several coatings can even be applied one after the other. Examples of coated fertilizer granules are found, for example, in DE 10 2005 028 016 A1. A detailed description of the determination of the biodegradability of organic polymers is found, for example, under "Castia Bastioli, Handbook of Biodegradable Polymers, Rapra Technology Limited, 2005, ISBN: 1-85957-389-4, chapter 5, pages 145-181" and in the described standards ISO 14852, ISO 14851, ISO 14855, ISO 14855 Amendment 1, EN 13432, DIN V54900, ASTM D6002-96, ASTM D6400-99.

The selection of a suitable polymer for the appropriate fertilizer granule is, however, associated with some difficulties. For example, as described in U.S. Pat. No. 5,766,637 A in column 1, the polymer can be melted, polymerized or dissolved. The application of a polymer in a solvent is certainly the commonest and technically simplest use.

Since the fertilizer granules are then applied to the soil and can even at least theoretically accumulate, with other parts of the coating and/or solvents used, in the plants to be treated with fertilizer, only selected solvents which are not harmful to health and/or the environment may be used. Suitable solvents for polymers, for example chlorine-containing solvents, such as DCM (dichloromethane) or TCM (trichloromethane), must not be used at all in agriculture. Naturally, in the field of organic solvents, this classification into harmful to health or not harmful to health can be carried out only with difficulty. In addition, in the course of the ever stricter environmental regulations, an increase in the classification of solvents as "harmful to health" can be assumed. In addition to the accumulation in the soil, organic solvents, especially volatile organic solvents "VOCs" (volatile organic compounds), also place special demands on the actual coating process. The formation of explosive mixtures as well as the exposure of the employees must be taken into account.

U.S. Pat. No. 4,019,890 A discloses a process for coating fertilizer granules with a thermoplastic polymer. Polyolefins, such as, for example, polyethylene or polypropylene, are suitable as polymers and tetrachloroethylene, toluene, xylene or trichloroethylene are suitable as solvents.

WO 03/082003 A2 discloses a particulate, urea-containing fertilizer which makes possible a delayed release of nitrogen in the soil. The fertilizer comprises a core material and a coating based on a urea/formaldehyde polymer. The polymer is bound to the core material via a binder, for example a urea/formaldehyde resin.

U.S. Pat. No. 5,766,637 A discloses the microencapsulation of a core material in a polymer matrix. The polymer is mixed with the core material and the mixture is dissolved in supercritical CO$_2$. The resulting product contains the finely divided core material in the swollen polymer matrix.

EP 0 706 821 A1 discloses a process for the coating of microparticles. The process comprises the inclusion of an active compound in a casing. The process comprises the suspending of the active substance in a supercritical fluid containing the encasing material.

DE 10 2005 028 016 A1 discloses a fertilizer which exhibits a coating with a biodegradable or hydrolytically degradable oligomer or polymer, which makes possible a controllable release of active substance, which is greatly delayed in comparison with uncoated fertilizers.

Thus a need exists for coated fertilizer granules that can be produced without the use of solvents which are harmful to the environment and/or health. At the same time, the least possible cost-intensive additional equipment conversion measures should be required and additional logistical expenditure should be avoided.

DETAILED DESCRIPTION

Figure 1:
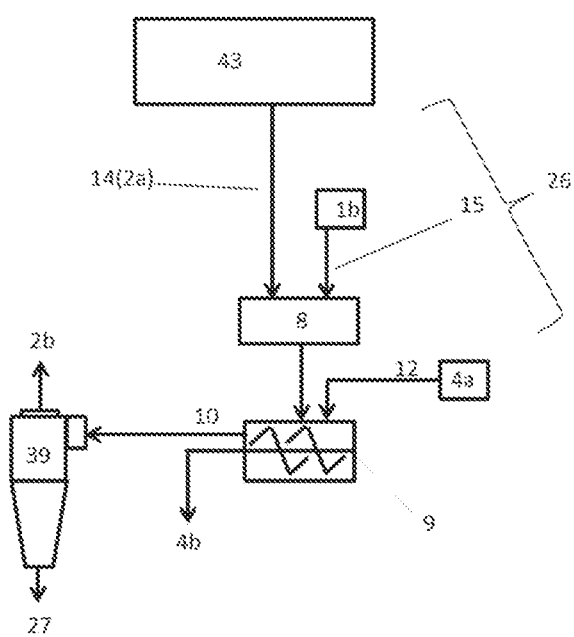
FIG. 1 is a diagrammatic cross-sectional view of an example plant complex for coating urea-containing granules.

Although certain example methods and apparatus have been described herein, the scope of coverage of this patent is not limited thereto. On the contrary, this patent covers all methods, apparatus, and articles of manufacture fairly falling within the scope of the appended claims either literally or under the doctrine of equivalents. Moreover, those having ordinary skill in the art will understand that reciting "a" element or "an" element in the appended claims does not restrict those claims to articles, apparatuses, systems, methods, or the like having only one of that element, even where other elements in the same claim or different claims are preceded by "at least one" or similar language. Similarly, it should be understood that the steps of any method claims need not necessarily be performed in the order in which they are recited, unless so required by the context of the claims. In addition, all references to one skilled in the art shall be understood to refer to one having ordinary skill in the art.

The invention further comprises a plant complex for the coating of urea-containing particles with biodegradable polymers. Additional advantageous embodiments are found in the respective dependent claims.

The invention further comprises the use of the plant complex according to the invention for the coating of urea-containing particles with biodegradable polymers.

The process according to the invention for the coating of urea-containing granules with organic polymers comprises at least the following steps. In a first step, supercritical carbon dioxide is provided. One advantage of the process is that an existing $CO_2$ compressor can be used and the $CO_2$ withdrawn as a partial flow at the existing pressures. The $CO_2$ is preferably provided in an ammonia-urea complex. Within the meaning of the invention, the expression "ammonia-urea complex" describes the combination of a plant for ammonia synthesis with a plant for urea synthesis. The supercritical carbon dioxide is provided by compressing the gaseous carbon dioxide and then condensing the carbon dioxide and preserving the liquid carbon dioxide. In the next step, the pressure and/or the temperature is increased above the critical point of carbon dioxide and a supercritical carbon dioxide is obtained. The supercritical carbon dioxide is preferably provided as follows. In a first step, gaseous carbon dioxide is compressed. Preferred pressure ranges include 20 bar to 35 bar. The previously compressed carbon dioxide is then preferably condensed in a condenser, for example with the aid of a suitable refrigerant (e.g. in an $NH_3$ refrigerating system; for other refrigerants see, for example, VDI Wärmeatlas, ISBN 978-3-642-19980-6). The carbon dioxide is preferably cooled to temperatures between −15° C. and −35° C. In the next step, the liquid carbon dioxide is preferably subjected to compression and a temperature increase. Both the pressure and the temperature are raised above the critical values (for pure carbon dioxide: $Tc=31.00°$ C., $pc=76.262$ bar, from Holleman, Wiberg, Lehrbuch der Anorganischen Chemie [Textbook of Inorganic Chemistry], 102th edition, 2007, page 894 (ISBN 978-3-11-017770-1); depending on the purity of the carbon dioxide, the critical temperature Tc and the critical pressure pc may differ therefrom) and supercritical carbon dioxide is obtained. The intermediate step via the above condensation stage, in comparison to the direct compression of the gaseous carbon dioxide, is, in terms of apparatus, a simpler, energy-saving and more reliable subsequent compression and temperature increase. In a second stage, an organic polymer, preferably a biodegradable organic polymer, is dissolved in the supercritical carbon dioxide and a polymer-containing solution is obtained. The expression "polymer-containing solution" includes, within the meaning of the invention, also polymer-containing suspensions and emulsions. The expression "biodegradable organic polymer" includes polymers which, according to at least one or more of the following standards ISO 14852, ISO 14851, ISO 14855, ISO 14855 Amendment 1, EN 13432, DIN V54900, ASTM D6002-96, ASTM D6400-99 can be degraded under to at least partial dissolution of their chemical structure. The expression "biodegradable organic polymer" preferably includes organic polymers which comply with a degradability according to EN 13432 of more than 50%, particularly preferably the standard EN 13432 with at least 90%. A detailed description of biodegradability is found as described above under "Castia Bastioli, Handbook of Biodegradable Polymers, Rapra Technology Limited, 2005, ISBN: 1-85957-389-4, chapter 5, pages 145-181". In a subsequent stage, the polymer-containing solution is mixed with urea-containing granules and the temperature and/or the pressure is lowered below the critical point of carbon dioxide.

The stage of "mixing" the granules with the polymer-containing solution is preferably carried out by spraying, particularly preferably in a drum coater or in a fluidized bed coater. With an abrupt drop in the pressure and the temperature, the polymer adheres and solidifies on the granules. The urea-containing granules preferably exhibit mean particle sizes of 0.5 mm to 10 mm, preferably 1 mm to 6 mm, particularly preferably of 2 mm to 4 mm. The mixing of the polymer-containing solution with urea-containing granules and the further reduction in temperature and/or in pressure can take place both in succession and simultaneously within the scope of the invention. An approximately simultaneous mixing and, for example, pressure reduction can be carried out, for example, by spraying the polymer-containing solution onto the urea-containing granules. Accordingly, the phase transition of the carbon dioxide from the supercritical state of aggregation to the gaseous state of aggregation can take place, for example, simultaneously with the spraying on or subsequently after mixing, for example by mixing or stirring. With the phase transition of the carbon dioxide (supercritical to gaseous), a parallel adhesion or coating of the polymer on the surface of the urea-containing granules could be ascertained; this process is similar to the evaporation of the solvent when spraying under normal pressure. In this mixing stage, for example by spraying on or stirring in, coated urea-containing granules and gaseous carbon dioxide are obtained in the course of the pressure reduction. The coated urea-containing granules preferably exhibit mean particle sizes of 0.5 mm to 10 mm, preferably 1 mm to 6 mm, particularly preferably of 2 mm to 4 mm.

The process is preferably characterized in that the supercritical carbon dioxide is provided in a connected industrial plant complex. The connection can be established using conventional connecting elements, pipes, compressors, pumps, etc. The expression "industrial plant complex" in the context of the invention includes urea synthesis plants, coking plants, refinery plants and/or an ammonia-urea complex. The carbon dioxide obtained in these plants can be used directly (preferably after purification) to produce supercritical carbon dioxide; long transportation routes and transportation devices are no longer necessary. The expression "supercritical carbon dioxide" within the meaning of the invention also includes supercritical solvents with a carbon dioxide content of >(greater than/equal to) 50 wt. % (weight percent) carbon dioxide.

As described above, the organic polymer preferably includes biodegradable polymers.

In a preferred embodiment, the biodegradable polymer includes polylactides (PLA), polyglycols, polycaprolactones, poly(hydroxybutyric acid), poly(hydroxyvaleric acid), polyalkyl terephthalates, polyanhydrides, poly(1,4-dioxane-2,5-diones), polyamino acids, peptides, polysaccharides, cellulose esters, cellulose hydrate, cellulose acetate, carboxymethyl cellulose, lignin, polyhydroxy fatty acids, starch, biodegradable polyesters, biodegradable polyamides, biodegradable polyimides, polyhydroxyalkanoates and polybutylene succinates (PBS), amylose, amylopectin and/or mixtures, oligomers, derivatives and/or copolymers thereof.

The polymer-containing solution preferably contains greater 20 wt. % to 70 wt. % biodegradable polymers, particularly preferably 40 wt. % to 60 wt. % biodegradable polymers.

The gaseous carbon dioxide is preferably returned to the process and converted into supercritical carbon dioxide. This recycling significantly reduces the carbon dioxide consumption and the energy and operating costs within the process according to the invention. Alternatively, waste disposal of the $CO_2$ is also possible. This primarily depends on local conditions, such as environmental regulations, operating costs and the technical expense of the recirculation.

The gaseous carbon dioxide and/or the supercritical carbon dioxide is preferably provided in a connected industrial plant complex, particularly preferably in a urea synthesis plant, ammonia synthesis plant, coking plant, refinery plant and/or in an ammonia-urea complex, particularly preferably an ammonia-urea complex. Within the meaning of the invention, the expression "ammonia-urea complex" denotes the combination of a (preferably locally connected) plant for ammonia synthesis with a plant for urea synthesis.

The ammonia synthesis plant provides the ammonia and at least part of the carbon dioxide.

The condensation described above preferably takes place with the aid of a coolant, in particular ammonia, particularly preferably with ammonia from a connected ammonia refrigerating system. For example, the ammonia obtained in the connected ammonia plant can be used as coolant.

Particularly preferably, the liquid carbon dioxide is subjected to a flash process for the removal and/or outgassing of inert and noncondensable gases.

The gaseous carbon dioxide is preferably compressed in a first step A in an LP (low-pressure) compression step (preferred pressure ranges from 5 bar to 10 bar) and, in a second step B, in an HP (high-pressure) compression step (preferred pressure ranges from 20 bar to 30 bar). The LP (low-pressure) compression step and the HP (high-pressure) compression step are particularly preferably located in one housing.

A cold/heat recovery and/or cooler are particularly preferably provided for in the following process stages:
before the first step A;
between the first step A and the second step B; and/or
after the second step B.

The expression "cold/heat recovery" includes, within the meaning of the invention, heat exchangers and similar devices conventional to a person skilled in the art.

In a preferred embodiment, the urea-containing granules and/or the coated urea-containing granules contain ammonium salts, nitrates, phosphates, sulfur, potassium, calcium, preferably urea, ammonium sulfate, ammonium nitrate, phosphates, sulfur and/or mixtures thereof.

The urea-containing granules preferably exhibit a mean particle size of 0.5 mm to 8 mm, particularly preferably of 1 mm to 6 mm, especially preferably of 2 mm to 4 mm.

The polymer-containing solution is preferably mixed with the urea-containing granules in one or more coaters, preferably drum coaters, fluidized bed coaters, and/or fluidized bed coaters with tangential spraying.

The invention further includes a plant complex for the coating of urea-containing granules at least including a urea synthesis plant, optionally a connected ammonia synthesis plant and a plant for the coating of urea-containing granules/particles. The ammonia synthesis plant and the urea synthesis plant are preferably combined in an ammonia-urea complex. The expression "ammonia-urea complex" denotes, within the meaning of the invention, at least two plants—each for ammonia and urea synthesis—which more often than not are located in close proximity to one another and more often than not are operated using shared offsites and utilities. The carbon dioxide is preferably provided in the ammonia synthesis plant and compressed in the urea synthesis plant and converted into supercritical $CO^2$. The expression "granules" includes, within the meaning of the invention, particles, granules, agglomerates, preferably in the range of a mean particle diameter of 0.1 mm to 10 mm. Ammonia synthesis plants are known to a person skilled in the art, and the ammonia is preferably generated in principle as, for example, described by Holleman, Wiberg, Lehrbuch der Anorganischen Chemie [Textbook of Inorganic Chemistry], 102th Edition, 2007, pages 662-665 (ISBN 978-3-11-017770-1), based on the "Haber-Bosch process", from the elements according to equation (1):

$$3H_2 + N_2 \rightleftharpoons 2NH_3 + 92.28 \text{ kJ} \tag{1}$$

The starting material nitrogen ($N_2$) can be obtained, for example, by low-temperature air separation or by reduction of oxygen in the air. The hydrogen is preferably obtained via the "steam reforming process" according to equation (2):

$$C_nH_{2m} + nH_2O \rightleftharpoons (n+m)H_2 nCO \tag{2}$$

In the subsequent "carbon dioxide conversion", a further conversion takes place according to equation (3):

$$CO + H_2O \rightleftharpoons CO_2 + H_2 \tag{3}$$

The carbon dioxide ($CO_2$) produced according to equation (3) preferably serves as carbon dioxide source for obtaining the supercritical carbon dioxide as described above and below. Reaction conditions, suitable catalysts and alternative processes are found, for example, on pages 663 to 664 of the Holleman, Wiberg, Lehrbuch der Anorganischen Chemie [Textbook of Inorganic Chemistry], cited above.

The plant complex according to the invention furthermore includes at least one feed line for supercritical carbon dioxide from the urea synthesis plant and one feed line for a biodegradable polymer. Furthermore, a mixing device for supercritical carbon dioxide and the biodegradable polymer is included, which is connected to the feed line for the supercritical carbon dioxide and to the feed line for the biodegradable polymer. The outlet of the mixing device and a feed line for urea-containing granules are connected to a coater. The coater exhibits a first outlet for gaseous carbon dioxide and a second outlet for a coated product made of urea-containing granules and a biodegradable polymer casing. Within the meaning of the invention, the coater preferably includes pressure- and temperature-resistant stirring and mixing devices, coaters and spraying devices. The expression "connected" includes, within the meaning of the invention, pipes, connecting elements, pumps, compressors, etc, known to a person skilled in the art, which make possible transportation of gases, liquids, solids and mixtures thereof.

One with an ammonia synthesis unit as part of an ammonia-urea complex and/or a urea granulation plant is preferably included. The urea granulation plant preferably includes fluidized bed granulation and/or prilling plants. The above combination makes possible local preparation of the coated urea-containing granules at one place and without additional logistics costs.

The first outlet for gaseous carbon dioxide of the coater is preferably connected to a dust scrubber, dust separator and/or cyclone. With the aid of the abovementioned devices, the dust emissions can be reduced when the carbon dioxide is released into the atmosphere (without recycling the carbon dioxide).

A carbon dioxide compression step is preferably included within the urea synthesis plant. The ammonia is preferably provided and generated in an ammonia synthesis plant. This makes it possible for supercritical carbon dioxide to be provided in the urea synthesis plant. It can be provided without relatively major conversion measures in the urea synthesis plant and the pressure and compression devices available there. The supercritical carbon dioxide can preferably be provided both by elements of the urea synthesis plant and of the ammonia synthesis plant.

The carbon dioxide compression step within the urea synthesis plant preferably includes at least one carbon dioxide CO2 feed line connected to a (with the pressure increasing from the first to the fourth step) first compression step (preferred pressure ranges from 5 bar to 10 bar) and a second compression step (preferred pressure ranges from 20 bar to 30 bar) connected to the first compression step. A third compression step (preferred pressure ranges from 70 bar to 90 bar) connected to the second compression step and a fourth com press ion step (preferred pressure ranges from 140 bar to 180 bar) connected to the third compression step. The compression steps comprise both individual compressors and combinations of respective low-pressure (LP) and high-pressure (HP) steps within a housing. The first and second compression steps preferably form a low-pressure (LP) and high-pressure (HP) step within a first housing. Furthermore, the third and fourth compression steps preferably form a low-pressure (LP) and high-pressure (HP) step within a second housing. The housings (first and/or second housing) are preferably driven by a turbine. In an optional embodiment, a first connecting line to an optional urea synthesis plant connected to the fourth compression step is included. This makes possible use of the compressed carbon dioxide in the synthesis of urea according to the simplified equations (5) and (6): [from Ullmann's Encyclopedia of Industrial Chemistry, Introduction, 2010, DOI:

$$2NH_3 + CO_2 \rightleftharpoons H_2N\text{—}COONH_4 \quad (5)$$

$$H_2N\text{—}COONH_4 \rightleftharpoons (NH_2)_2CO + H_2O \quad (6)$$

The plant complex according to the invention includes a branch between the second compression step and the third compression step. Starting from the branch, a second connecting line leads to a degassing system, the second connecting line running through a refrigerating system upstream of the degassing system (being continuously connected).

The refrigerating system makes possible liquefaction of the gaseous carbon dioxide. The degassing system, preferably a flash drum or gas-liquid separator, makes possible the removal/reduction of inert gases, for example argon and nitrogen. A pump is connected to the degassing system and makes possible an increase in pressure of the liquid carbon dioxide to preferably 100 bar to 250 bar, particularly preferably 150 bar to 200 bar. The expression "pump", for example a plunger pump, includes, within the meaning of the invention, pumps (and compressors) known to a person skilled in the art for increasing the pressure of liquids (and/or gases) and/or supercritical fluids and/or mixtures thereof. A third connecting line is connected to the pump and to the feed line (the plant complex for the coating of urea-containing granules) for supercritical carbon dioxide. Preferably, by increasing the pressure and/or the temperature, the liquid carbon dioxide is converted into supercritical carbon dioxide in the third connecting line and in the associated areas. Particularly preferably, only the temperature is increased. For this purpose, heat exchangers and/or heaters, for example, can preferably be provided in the third connecting line. Preferably, the cold of the liquid $CO_2$, after the separation of inert substances in the degassing system and after the compression with the pump, is used for the further cooling of the gas ($CO_2$) before the intake point of the second compression step (after the cooler intrinsic to the process, e.g. interstage cooler). The preheated liquefied $CO_2$ is preferably used for the further cooling of the gas upstream of the intake point of the first compression step (after the cooler intrinsic to the process) and is then brought to the target temperature using the heat of the material flow after the second compression step. The order in which the cold is integrated (for example through coolers, heat exchangers, heaters) can also be changed as required, i.e. first before the first compression step and then before the second compression step.

In a preferred embodiment, elements for cold/heat recovery and/or coolers are included within the ammonia synthesis plant and urea synthesis plant) (ammonia-urea complex) in one or more of the following elements:
the carbon dioxide $CO_2$ feed line;
between the first compression step and the second compression step;
between the second compression step and the third compression step;
between the third compression step and the fourth compression step; and/or
the first connecting line.

The expression "cold/heat recovery" includes, within the meaning of the invention, heat exchangers, coolers, heaters and similar devices conventional to a person skilled in the art. Depending on the exact design of the process, targeted temperature control and the recovery of excess amounts of heat are possible. This recovery lowers the process costs and required process resources.

A passivation air feed line is preferably arranged between the second compression step and the third compression step, which is required, for example, in a downstream hydrogen $H_2$ removal reactor and in the urea synthesis. For example, the passivation air provides oxygen for the catalytic reaction (7)

$$H_2 + O_2 \xrightarrow{\text{Cat.}} H_2O \quad (7)$$

and for the formation of the oxide layer in the high-pressure and high-temperature region of the urea synthesis. The passivation air feed line is arranged in the process direction behind the branch for removal of the gaseous $CO_2$ for the subsequent conversion into supercritical $CO_2$ between the second compression step and the third compression step. This avoids contamination of the gas flow branched off for the formation of the supercritical $CO_2$.

The invention further comprises the use of the plant complex according to the invention for the coating of urea-containing particles with biodegradable polymers.

FIG. 1 shows a diagrammatic cross section of the plant complex according to the invention for the coating of urea-containing granules at least including an ammonia-urea complex (43) and a plant for the coating of urea-containing granules (26). The supercritical carbon dioxide (2a) obtained in the ammonia-urea complex (43) arrives via the feed line for supercritical carbon dioxide (14) from the ammonia-urea complex (43) together with a feed line (15) for a biodegradable polymer (1b) in a mixing device (8). A feed line for urea-containing granules (13) and a feed line from the mixing device (8) with the biodegradable polymer (1b) dissolved in the supercritical carbon dioxide are connected to a coater (9), for example a drum coater, fluidized bed coater, and/or fluidized bed coater with tangential spraying. The coater includes a first outlet (10) for gaseous carbon dioxide (2b) and a second outlet for the coated product (4b). The first outlet (10) for gaseous carbon dioxide (2b) is connected to a dust scrubber, dust separator and/or cyclone (39). The collected dust particles (27) can alternatively be disposed of as waste or returned to the process. Most of the dust (probably) consists of polymer particles. These are preferably (not shown) washed with water, then evaporated and returned to the mixing device (8). This evaporation can take place in the urea synthesis plant. This flow tends to be rather small and can simply be added to the main evaporation. It is more likely that the polymer will not dissolve, so that no evaporation, but possibly drying, is necessary.

Figure 2:
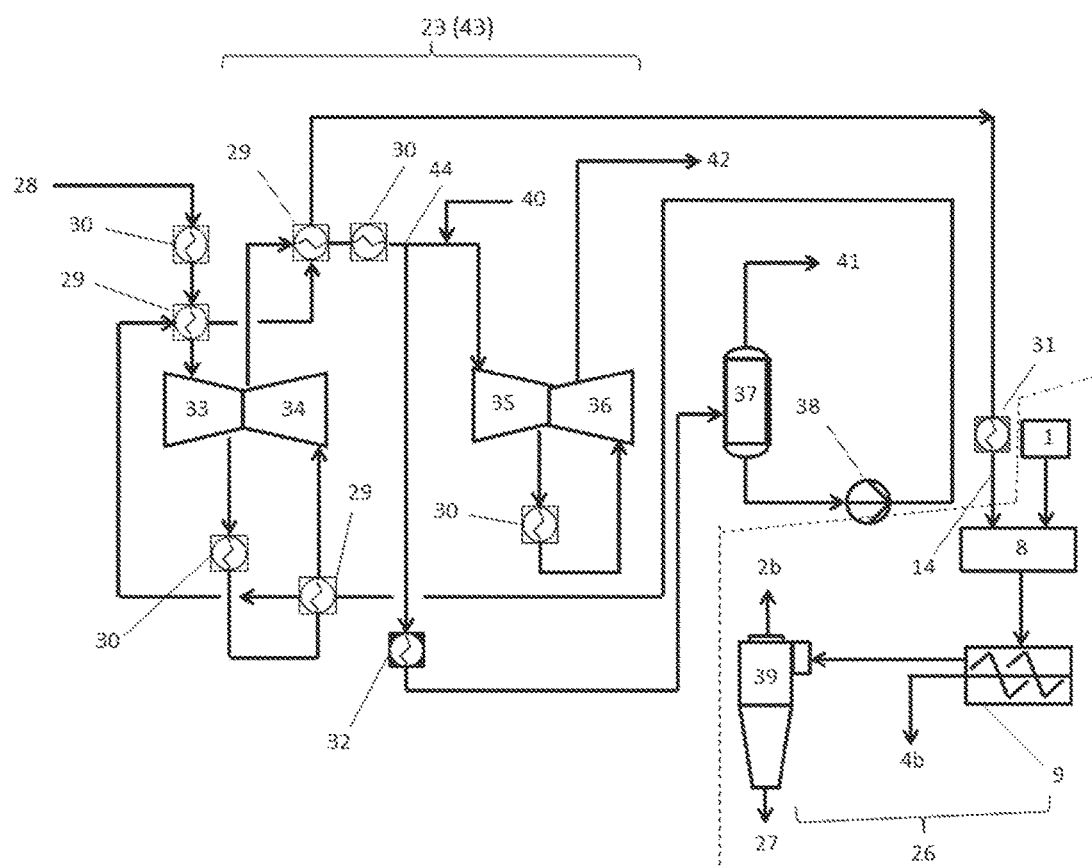
FIG. 2 is another diagrammatic cross-sectional view of an example plant complex for coating urea-containing granules and of an example sector from the ammonia-urea complex.

FIG. 2 shows a further diagrammatic cross section of the plant complex according to the invention for the coating of urea-containing granules (26) and a sector from the ammonia-urea complex (43). Carbon dioxide, preferably carbon dioxide from the carbon dioxide scrubbing of the steam reforming process, is, in the carbon dioxide compression step shown within the ammonia-urea complex (43), introduced via at least one carbon dioxide $CO_2$ feed line (28) into a (with the pressure increasing from the first to the fourth step) first compression step (33) (preferred pressure ranges from 5 bar to 10 bar), a second compression step (34) (preferred pressure ranges from 20 bar to 30 bar), a third compression step (35) (preferred pressure ranges from 70 bar to 90 bar) and a fourth compression step (36) (preferred pressure ranges from 140 bar to 180 bar). A first connecting line (42) is connected from the fourth compression step (36) to a urea synthesis unit. Within the meaning of the invention, the expression "urea synthesis unit" includes the reactors and feed lines provided within the urea synthesis plant for the actual synthesis of urea from $CO_2$ and $NH_3$. This connection makes it possible for the compressed carbon dioxide to be used in the synthesis of urea. The plant complex according to the invention includes a branch (44) between the second compression step (34) and the third compression step (35). Starting from the branch (44), a second connecting line leads to a degassing system (37), the second connecting line running through a refrigerating system (32) upstream of the degassing system (37) (being continuously connected). The refrigerating system (32) makes possible liquefaction of the gaseous carbon dioxide. The degassing system (37) makes possible the removal/ reduction of inert gases, for example argon, noncondensable components of $CO_2$ and nitrogen, via the exhaust air line (41). A pump (38) is connected to the degassing system and makes possible an increase in pressure of the liquid carbon dioxide to 150 bar to 200 bar. A third connecting line is connected to the pump (38) and the feed line (14) for supercritical carbon dioxide. Preferably, by increasing the temperature, the liquid carbon dioxide (2c) is converted into supercritical carbon dioxide (2a) in the third connecting line and in the associated areas. Elements for cold/heat recovery (29) and/or coolers (30) and/or heaters (31) are included in the following elements: the carbon dioxide $CO_2$ feed line (28), between the first compression step (33) and the second compression step (34), between the second compression step (34) and the third compression step (35), between the third compression step (35) and the fourth compression step (36); and/or the first connecting line (42) to the urea synthesis plant. Preferably, the first cooler (30) in the flow direction of the $CO_2$ feed line (28) belongs to the ammonia synthesis plant, and the remaining elements for generating the supercritical carbon dioxide belong to the urea synthesis plant. A passivation air feed line (40) is arranged between the second compression step (34) and the third compression step (35), which is required, for example, in a downstream hydrogen $H_2$ removal reactor (not shown) and in the urea synthesis. The structure described in FIG. 1 is connected via the supply line for supercritical carbon dioxide (14).

LIST OF REFERENCE INDICATIONS (1) organic polymer
(1b) biodegradable polymer
(2a) supercritical carbon dioxide
(2b) gaseous carbon dioxide
(3) polymer-containing solution
(4a) urea-containing granules
(4b) coated urea-containing granules
(8) mixing device
(9) coater
(10) outlet for gaseous carbon dioxide
(11) outlet for coated product
(12) feed line for urea-containing granules
(14) feed line for supercritical carbon dioxide
(15) feed line (15) for the biodegradable polymer
(23) carbon dioxide compression step
(26) plant for the coating of urea-containing particles/ granules
(27) dust particles
(28) $CO_2$ feed line (28) connected to a first compression step
(29) elements for cold/heat recovery (29)
(30) cooler
(31) heater/heating element
(32) refrigerating system/cooler
(33) first compression step
(34) second compression step
(35) third compression step
(36) fourth compression step
(37) degassing system
(38) pump
(39) dust scrubber, dust collector, acid scrubber and/or cyclone
(40) passivation air feed line
(41) exhaust air line
(42) first connecting line to a urea synthesis unit
(43) ammonia-urea complex

What is claimed is:

1. A process for coating urea-containing granules with organic polymers, the process comprising:

compressing and condensing gaseous carbon dioxide to obtain liquid carbon dioxide, wherein the compressing of the gaseous carbon dioxide occurs in a first step in a low-pressure compression step and in a second step in a high-pressure compression step, wherein the low-pressure includes from 5 bar to 10 bar and the high-pressure includes from 20 bar to 35 bar;

increasing at least one of pressure or temperature above a critical point of carbon dioxide to obtain supercritical carbon dioxide;

dissolving an organic polymer in the supercritical carbon dioxide to obtain a polymer-containing solution; and mixing the polymer-containing solution by at least one of spraying the polymer-containing solution onto or bringing the polymer-containing solution into contact with urea-containing granules, in which a simultaneous or subsequent lowering of temperature and/or pressure below the critical point of carbon dioxide occurs, and coated urea-containing granules and gaseous carbon dioxide are obtained.

2. The process of claim 1 wherein the organic polymer includes biodegradable polymers.

3. The process of claim 2 wherein the biodegradable polymer includes polylactides (PLA), polyglycols, polycaprolactones, poly(hydroxybutyric acid), poly(hydroxyvaleric acid), polyalkyl terephthalates, polyanhydrides, poly(1,4-dioxane-2,5-dione), polyamino acids, polysaccharides, cellulose esters, cellulose hydrate, cellulose acetate, carboxymethyl cellulose, lignin, polyhydroxy fatty acids, starch, biodegradable polyesters, biodegradable polyamides, biodegradable polyimides, polyhydroxyalkanoates and polybutylene succinates (PBS), amylose, amylopectin, and/or mixtures, oligomers, derivatives, and copolymers thereof.

4. The process of claim 1 wherein the polymer-containing solution contains between 20 to 70% by weight biodegradable polymers.

5. The process of claim 1 comprising returning the gaseous carbon dioxide to the compressing and condensing step and converting the gaseous carbon dioxide to supercritical carbon dioxide.

6. The process of claim 1 comprising providing the gaseous carbon dioxide and the supercritical carbon dioxide in a connected industrial plant complex.

7. The process of claim 1 wherein the condensation occurs with the aid of ammonia from a connected ammonia refrigerating system.

8. The process of claim 1 comprising subjecting the liquid carbon dioxide, after the compressing and condensing, to a flash process for at least one of removal or outgassing of inert, non-condensable gases.

9. The process of claim 1 wherein a cold/heat recovery and/or cooler are provided at least one of before the first step, between the first and second steps, or after the second step.

10. The process of claim 1 wherein the urea-containing granules and/or the coated urea-containing granules contain at least one of, nitrates, phosphates, potassium, calcium, or sulfur.

11. The process of claim 1 wherein the urea-containing granules have a mean particle size of 0.5 to 8 mm.

12. The process of claim 1 comprising mixing the polymer-containing solution with the urea-containing granules in one or more coaters with tangential spraying.

13. The process of claim 1 wherein the first and second compression steps occur within a first housing.

* * * * *